US010722586B2

(12) United States Patent
Vendrusculo et al.

(10) Patent No.: US 10,722,586 B2
(45) Date of Patent: Jul. 28, 2020

(54) FILMOGENIC COMPOSITIONS FOR TOPICAL ANAESTHETIC BIOADHESIVES—TABS, FOR CONTROLLED RELEASE OF ACTIVE PRINCIPLES AND TOPICAL ANAESTHETIC BIOADHESIVES

(71) Applicant: UNIVERSIDADE FEDERAL DE PELOTAS, Pelotas (BR)

(72) Inventors: Claire Tondo Vendrusculo, Ribeirão Preto (BR); Angelita Da Silveira Moreira, Pelotas (BR); Adriana Fernandes Da Silva, Pelotas (BR); Evandro Piva, Pelotas (BR); Wellington Luiz De Oliveira Rosa, Pelotas (BR); Francisco Augusto Burket Del Pino, Pelotas (BR)

(73) Assignee: UNIVERSIDADE FEDERAL DE PELOTAS, Pelotas (BR)

( * ) Notice: Subject to any disclaimer, the term of this patent is extended or adjusted under 35 U.S.C. 154(b) by 0 days.

(21) Appl. No.: 15/525,481

(22) PCT Filed: Nov. 9, 2015

(86) PCT No.: PCT/BR2015/050210
§ 371 (c)(1),
(2) Date: May 9, 2017

(87) PCT Pub. No.: WO2016/074055
PCT Pub. Date: May 19, 2016

(65) Prior Publication Data
US 2017/0326242 A1 Nov. 16, 2017

(30) Foreign Application Priority Data
Nov. 10, 2014 (BR) .......................... 1020140280090

(51) Int. Cl.
| | | |
|---|---|---|
| A61K 47/36 | (2006.01) | |
| A61K 6/00 | (2020.01) | |
| A61K 45/06 | (2006.01) | |
| A61K 31/245 | (2006.01) | |
| A61L 24/08 | (2006.01) | |
| A61K 9/06 | (2006.01) | |
| A61K 6/65 | (2020.01) | |
| A61K 6/69 | (2020.01) | |
| A61K 6/78 | (2020.01) | |
| A61K 9/00 | (2006.01) | |
| A61L 24/00 | (2006.01) | |
| A61L 24/04 | (2006.01) | |
| A61K 47/00 | (2006.01) | |

(52) U.S. Cl.
CPC ................ *A61K 47/36* (2013.01); *A61K 6/00* (2013.01); *A61K 6/65* (2020.01); *A61K 6/69* (2020.01); *A61K 6/78* (2020.01); *A61K 9/006* (2013.01); *A61K 9/06* (2013.01); *A61K 31/245* (2013.01); *A61K 45/06* (2013.01); *A61L 24/0015* (2013.01); *A61L 24/043* (2013.01); *A61L 24/08* (2013.01); *A61K 47/00* (2013.01); *A61L 2300/402* (2013.01)

(58) Field of Classification Search
None
See application file for complete search history.

(56) References Cited

U.S. PATENT DOCUMENTS

| | | | |
|---|---|---|---|
| 4,894,232 A * | 1/1990 | Reul ...................... | A61K 9/006 424/439 |
| 5,618,563 A | 4/1997 | Berde et al. | |
| 5,672,356 A | 9/1997 | Rault et al. | |
| 5,912,271 A | 6/1999 | Brodin et al. | |
| 6,214,387 B1 | 4/2001 | Berde et al. | |
| 6,509,028 B2 | 1/2003 | Williams et al. | |
| 8,568,788 B2 | 10/2013 | Junior et al. | |
| 9,283,177 B2 | 3/2016 | Cohen et al. | |

(Continued)

FOREIGN PATENT DOCUMENTS

| | | |
|---|---|---|
| BR | PI 8805325 | 5/1990 |
| BR | PI 0406117 | 7/2006 |

(Continued)

OTHER PUBLICATIONS

International Search Report dated Dec. 23, 2015 in Corresponding International Application No. PCT/BR2015/050210.
Gupta, et al, "Buccal adhesive dosage forms: research to market", 2010, pp. 1-12, vol. XXV, The Pharmstudent.
Burgalassi, et al, "Development and in vitro/in vivo testing of mucoadhesive buccal patches releasing benzydamine and lidocaine", 1996, pp. 1-7, vol. 133, International Journal of Pharmaceutics.

(Continued)

*Primary Examiner* — Jessica Worsham
(74) *Attorney, Agent, or Firm* — B. Aaron Schulman, Esq.; Stites & Harbison, PLLC (57) ABSTRACT

Filmogenic compositions are described for topical anaesthetic bioadhesives (TABs) comprising a) a xanthan biopolymer matrix selected from *Xanthomonas* species and pathovars, including *Xanthomonas campestris* pathovars *campestris* and *maninhotis*, and *Xanthomonas arboricola* pathovar *pruni*, a producer of *pruni* xanthan, wherein the matrix is made of pure or combined xanthan varieties in any proportion, said matrix comprising between 1% and 95% by weight of the total weight of the composition, and additives or excipients; b) at least one anaesthetic, in a proportion of 0.1% to 50% by weight of the total weight of the composition. The topical anaesthetic bioadhesives (TABs) are also described, and they may be applied to the gingival mucosa and/or alveolar mucosa on the buccal (1) or lingual/buccal (2) surfaces with extensions and anatomical contours for crowns of the upper and lower dental arches.

20 Claims, 6 Drawing Sheets

(56) References Cited

U.S. PATENT DOCUMENTS

| | | |
|---|---|---|
| 2002/0013331 A1 | 1/2002 | Williams et al. |
| 2002/0192288 A1 | 12/2002 | Williams et al. |
| 2003/0027833 A1 | 2/2003 | Cleary et al. |
| 2003/0124190 A1 | 7/2003 | Williams et al. |
| 2005/0152957 A1 | 7/2005 | Cleary et al. |
| 2007/0042027 A1 | 2/2007 | Haley |
| 2007/0280972 A1 | 12/2007 | Zhang et al. |
| 2008/0064073 A1 | 3/2008 | Vendruscolo et al. |
| 2008/0242731 A1 | 10/2008 | Vancaillie et al. |
| 2009/0048347 A1 | 2/2009 | Cohen et al. |
| 2010/0086614 A1 | 4/2010 | Junior et al. |
| 2010/0092546 A1 | 4/2010 | Gurtner et al. |
| 2011/0288508 A1* | 11/2011 | McCarron ............ A61K 9/7053 604/307 |
| 2011/0315151 A1 | 12/2011 | Schabert |
| 2012/0034307 A1 | 2/2012 | Alam et al. |
| 2012/0083452 A1 | 4/2012 | Perricone |

FOREIGN PATENT DOCUMENTS

| | | |
|---|---|---|
| BR | PI 0704542-5 | 1/2009 |
| BR | PI 0701765-0 | 3/2009 |
| BR | PI 1004194-0 | 3/2012 |
| CN | 102406609 | 10/2014 |
| JP | H09255565 | 9/1997 |
| WO | WO-99/36071 | 7/1999 |
| WO | WO-01/02477 | 1/2001 |

OTHER PUBLICATIONS

Jaiswal, et al, "Oral strip technology: A review", 2014, pp. 130-143, vol. 2, No. 2, Indian Journal of Pharmaceutical and Biological Research.

* cited by examiner

FILMOGENIC COMPOSITIONS FOR TOPICAL ANAESTHETIC BIOADHESIVES—TABS, FOR CONTROLLED RELEASE OF ACTIVE PRINCIPLES AND TOPICAL ANAESTHETIC BIOADHESIVES

FIELD OF THE INVENTION

The invention belongs to the field of health, specifically to the pharmaceutical industry, with application in dental areas, medical and other interests, particularly for the prevention and control of localized and superficial pain in the region of the mouth and upper digestive tract, including the esophagus, through compositions for the preparation of bioadhesive topical anesthetic (BAT) for the controlled release of active principles, the filmogenic compositions containing a biocompatible and biodegradable biopolymer matrix, the xanthan gum being the primary constituent of the matrix.

BACKGROUND OF THE INVENTION

Local anesthesia is a pain control method most used in dentistry, one of the most feared procedures of dental practice, probably due to the perception of pain during needle insertion. Fear and anxiety associated with the anticipation of painful sensations represent barriers to dental care.

One of the most common techniques used to avoid or minimize discomfort induced by the application of local anesthesia involves the use of topical anesthetics prior to needle puncture. Despite the relative effectiveness obtained with this technique, the fear of pain and needles are still common, probably because the topical anesthetic does not guarantee full effectiveness. Because of this, well-defined and safe anesthetic techniques, associated with the use of effective anesthetics, may provide a more adequate pain control during dental care, especially in pediatric patients.

The effectiveness of topical anesthetics depends on some factors such as the anesthetic agent used, the topical anesthetic application time, the contact time, the application site and type of mucosa, the pharmaceutical topical anesthetic form (adhesive solution or mouthwash, gel or other forms), the diameter of the needle used, and the depth of penetration of the needle, among others.

The use of topical local anesthesia before the injection of local infiltrative anesthesia is the main method used to minimize the pain of needle insertion, so the anesthetic should have a faster onset of action and have sufficient length and penetration to be effective as a topical anesthetic.

Topical anesthetics were developed to relieve pain, especially in dental procedures. However, new uses for these anesthetics were added, such as sprays for use in the mouth and throat, gels used for pain relief in conditions like appearance of the teeth, gels and mouthwashes for use in canker sores, mouth irritation and gums, gels and ointments for use in the region of the lips and oral solutions for local anesthesia of the larynx, pharynx and esophagus to be ingested prior to performing certain medical tests and procedures.

Also in dentistry, more recently, specific products in the form of waxes or masses have been developed to prevent, and in some cases, treat lesions caused by braces or bands of tethers.

Because of its rapid onset of action (30 seconds on average), acceptable taste and low systemic absorption, the gel with 20% benzocaine has been a widely used anesthetic agent, especially in pediatric dentistry. Despite these advantages, adverse reactions such as methemoglobinemia have been documented after topical benzocaine.

Lidocaine is not associated with methemoglobinemia, a condition which involves iron ion oxidation of ferrous state ($Fe^{2+}$) to the ferric state ($Fe^{3+}$), making the hemoglobin molecule incapable of carrying oxygen.

For this reason, the products developed for use in pediatric dentistry must take into account, mainly the toxic potential of the anesthetics used, to avoid the types of unwanted reactions that may occur during or after the dental procedure.

The main local anesthetics currently used belong to two groups of substances, amides and esters. The group of amides is the most used, with its main anesthetics: lidocaine (Xylocaine), bupivacaine, levobupivacaine, prilocaine, mepivacaine, and ropivacaine.

In the group of the main anesthetic esters are tetracaine, benzocaine, procaine (Novocaine) and propoxycaine. There is also the articaine, the sole representative of the amide group with a thiophene grouping, discovered more recently.

Also in relation to the characterization of the anesthetics currently used in dentistry, tertiary amines with hydrophilic and lipophilic properties stand out for being a less toxic alternative, being more effective and having low allergenic potential than ester-type anesthetics, although they have been synthesized for a longer time in the 1940s. Ropivacaine and levobupivacaine are safer alternatives to bupivacaine because it has lower systemic toxicity.

One of the problems presented by local anesthetics is that they can cause mild to severe reactions. The most frequent reactions to these anesthetics are vaso-vagal, which can cause sweating, malaise, tachycardia, fainting and results to a neuro-vegetative reaction derived from fear, anxiety or panic.

The toxic reactions result from the use of excessive amount of anesthetic or accidental introduction in the blood vessels of the numbed region; these constitute the majority of the reactions described, with no allergic mechanism.

Allergic reactions, although rare (about 1%) may be more severe and intense. The most common is allergic contact dermatitis which resulting from a topical application on skin and mucous membranes of the anesthetic in the form of creams, ointments, gels and solutions. Allergic reactions to topical anesthetics can be prevented through clinical evaluation and analysis of the previous episode, then performing a skin test with the alternative anesthetic. Generally, lidocaine is used as an allergy test because of its widespread use and low incidence of reactions. The use of topical anesthetics is contraindicated for children under 2 years of age, especially in large areas (except for cases where there is strict professional supervision) in people with previous reports of hypersensitivity to benzocaine or other topical anesthetic of the ester type and in patients with severe burn at the site to be treated.

There are cases where the risks and benefits should be assessed in order to decide whether or not to use these drugs. The FDA has new restrictions on the use of certain anesthetics. Benzocaine is one it was found that it could lead to a problem called hemoglobinemia, which is a serious and potentially fatal adverse reaction. The target hemoglobinemia may occur minutes or hours after the application of benzocaine, even in the first application; it is most common in children under 2 years of age or younger.

In search of an ideal topical anesthetic, research results have shown the effectiveness of EMLA® (AstraZeneca™), formed by the eutectic mixture of lidocaine and prilocaine, both at 2.5%. Although this is not an anesthetic injection indicated for dental use, topical application in the oral mucosa has allowed the execution of procedures such as periodontal instrumentation, dentistry and, in some cases, extraction of deciduous and pulp therapies in pediatric dentistry and even biopsies.

The EMLA® also reduces the discomfort of intraligamentary injections and punctures in the palatal mucosa. A review of the literature from 1985 has shown that although the EMLA® provides analgesia in the most effective oral mucosa than topical anesthetics commercially available for dental use also has significant adverse effects: the main ones are bitter taste, burning sensation in the mucosa; and in some cases, it can cause allergic dermatitis, contact urticaria, and intense inflammatory reaction; and the high cost.

Although traditional topical anesthetics actually reduce the discomfort associated with needle insertion, the pain still felt and reported by patients undergoing this procedure is relevant, and this deserves the attention of researchers for the development of new and better products that enable an adequate and effective topical anesthesia.

Of all the regions of the oral cavity, the palatal mucosa is known for difficulty achieving adequate topical anesthesia. Obtaining effective topical anesthesia in the palatal mucosa is more difficult due to increased keratinization of this site and the presence of a dense connective tissue strongly adhered to the bone, making it difficult to stretch during the injection of the anesthetic solution. As the palatal mucosa is one of the most sensitive and painful areas of the oral cavity, the evaluation model of topical anesthesia on this site is the biggest challenge that a topical anesthetic can be submitted to. Thus, a topical anesthetic able to eliminate or significantly reduce pain during needle puncture and injection of an anesthetic solution in this region will be a breakthrough for dentistry.

The literature reports the low efficacy of topical anesthetics on the palate, as exemplified by the topical anesthetic action of 20% benzocaine gel compared to placebo, for some authors is effective, while for others it does not show the divergence on in reducing patient discomfort to the puncture site on the palate. This demonstrates the need for greater investment or more research with a focus to solve or alleviate the pain during the dental procedure.

Positive results can arise from the discovery of new anesthetics associated between them, or by the use of more concentrated dosage forms of drugs currently used, but with absorption/action restricted to the site of interest.

Disorders like ulcers or varied etiology of lesions on the lips and oral mucous membranes or in the upper digestive tract, such as the throat and esophagus, are also causing considerable pain and suffering. For the lips and oral areas, a wide variety of anesthetic products are available that are added or not in the other classes of drugs, commercial or manipulated, formulated from what is pharmaceutically known as "Orabase", a kind of gel more palatable and a suitable constitution to use in the mouth or on the lips on repeated applications.

Current topical anesthetics intended for the oral region, in most cases, including those made in orabase, regardless of active anesthetic principles, are presented in the form of mouthwashes and solutions for application in the form of spray or gels and ointments, which generally are efficient as to its purpose as a topical anesthetic, but its use has the following drawbacks:

form of spreading—for the application of gels and ointments, using a spatula is needed or the tip of the finger or another suitable device, which does not always guarantee full hygiene;

need for removal of excess ointment or gel for subsequent insertion needle for the application of injectable local anesthetic—which is typically carried out using cotton, which possibly may leave residues in the mouth of the patient, which is uncomfortable;

uncertainty of doses and the difficulty of small areas affect limitation—the application in the form of mouthwashes and sprays practically precludes the use of precise doses and application reduces the site of interest.

Gels and ointments, although they may be applied on a greater control area, do not allow the use of accurate doses and even bring, on the other hand, the drawback of partially anesthetized area and inconveniently anesthetize other nearby areas, especially the cheek and tongue, due to the direct contact with the topical anesthetic or because of the spread of this to the surrounding areas, and can also generate what is called gustatory anesthesia; do not allow clear identification of the site that will later be numbed by the use of injectable anesthetics; do not allow the use of higher concentrations of anesthetic due to the ineffectiveness in controlling the dose used and the fact that topical anesthetics can cause serious side effects and adverse reactions.

For new forms of topical anesthetics to be considered, a development in this area should have characteristics such as precise control of doses; The greater speed and intensity of anesthetic action due to the possibility of using more concentrated forms; Efficient adhesion even in wet areas; And when necessary, a longer-lasting action of the topical anesthetic in controlled release function. They will constitute as a major breakthrough in relation to topical anesthesia of the mouth and upper digestive tract. It is also related to medical practices, dental or investments made by the patient.

Topical anesthetics are among the first pharmaceutical forms formulated with local anesthetics and are still being used.

The document WO 2010/008601 A1 reports a topical anesthetic solution with a drug delivery system for fast location anesthetic action. The drug delivery system described herein includes a topical anesthetic agent, an alkane diol, a fatty acid (or the corresponding alcohol) or ester with a lower melting temperature than 40° C., and a volatile solvent (such as an alcohol short chain with silicone).

Among the more recent patent documents, the published US patent application, US 2012/0083452A1 relates to liquefied compositions of local anesthetics for topical application that includes different anesthetics, Szeto-Schiller peptides, and a carrier for penetration such as lecithin, and may further contain a vasoconstrictor and tyrosine. More advanced controlled release systems may be used in the solutions.

The document EP 0,767,669 provides topical anesthetic pharmaceutical compositions in the form of an ointment or cream, which have one or more topical anesthetic agents, a polar lipid, a triacylglycerol and optionally water. The controlled release system of the invention is a nanoparticle encapsulated in a microparticle sensitive to moisture. The nanoparticles have a diameter of about 0.01 microns-to 10 microns, having a solid hydrophobic core and a positively charged bioadhesive/mucoadhesive surface. The invention also provides their use in oral hygiene products (such as toothpaste) and for the treatment and/or prevention of the periodontal disease, since the nanoparticles could also be effective for the release of biologically active substances into the periodontal pocket.

The use of the pharmaceutical gel has recently been the classic tool used to obtain a certain adhesion of the carrier vehicle for anesthetics for topical application to the site. Among the documents of general anesthetics use, the published US patent application US 2007/0280972 A1 foresees the use of an adhesive gel drug delivery system for the dermal tissue and may include medicine, solvent, and gelling agents. When applied on the skin, the compound can form a gel layer that solidifies after the evaporation of at least a part of the volatile gel system. Furthermore, the solidified gel layer could be removed even by washing with designated solvents.

Among the documents which relate to the use of topical anesthetics also for dental use is BR 0406117 document, which describes a gel for treatment of mouth ulcers with cicatrizing and anesthetic effect, especially for patients using orthodontic appliances and have thrush; Natrosol is composed of a gelling agent, glycolic extract of propolis, dexamethasone acetate, lidocaine, nipagin, nipazol and distilled water.

The published Brazilian document BR 0704542 A2 discloses a pharmaceutical composition for topical anesthetic gel directed to use in dental procedures, comprising a pharmaceutically effective amount of at least one anesthetic and a gelling agent. The invention would allow for greater penetration of the anesthetic through a stable viscosity that keeps the drug for a longer duration and at a higher concentration at the site of action; thus, increasing the duration of the anesthesia and reducing their toxicity.

To alleviate the pain for a longer time, the international publication WO 2002/000195A1 describes various anesthetic compositions in gel form for the injured mucosa due to abrasions, ulcerations, trauma or incisions. The compositions of this invention are particularly suitable for application to the mucosa of the oral cavity and nose as well.

The published US application US 2012/0034307A1 also involves the formulation of an aqueous gel and a method for inducing anesthesia. This US document describes a composition containing water, an anesthetic (such as lidocaine hydrochloride), the viscoelastic polymer hydroxypropylmethylcellulose, and a tonicity modifier.

In recent years, the encapsulation of anesthetic agents into liposomes has been described and studied, this includes the document CN 102406609, which relates to the use of lidocaine HCl liposome encapsulated in polymers. The encapsulation rate of the polymeric liposome was between 60 and 85%, while the diameter of the grain that liposome would lie between 60 and 180 nm. The lidocaine hydrochloride may be applied directly to the skin surface, mucous membrane, or be in the form of a gel or an ointment.

Alternatively, the anesthetic can be incorporated into nanoparticles. The uses of polymeric nanoparticles are provided in the International publication WO 2008/113144A1, which describes nanoparticulate anesthetic compositions for topical use wherein at least one anesthetic agent would be encapsulated in polymeric nanoparticles suspended in the hydrogel and could be applied topically, both on the skin and mucosa.

Topical anesthetic preparations in gel form can also be embedded or attached to inert carriers, occlusive or not. International Publication WO 2001/002477A1 relates to the use of a compound containing a self-adhesive pre-formed layer of gel for topical application, containing less than 10% of a mixture of polysaccharides consisting of gellan gum; xanthan gum is a polysaccharide mannosylated (this selected from a galactomannan or glucomannan derivative, or mixtures thereof). Still possess about 30% to 99.5% water, wherein the compound comprises less than 10% total polysaccharide. The product would be suitable for topical use, is easy to use, is discreet, and would be in accordance with the contours of the surface target when applied.

The international publication WO 2002/89849A1 relates to a pharmaceutical anesthetic composition for topical administration. The composition comprises, besides a therapeutically effective amount of the anesthetic, a vehicle that does not trigger liposomal release thereof, consisting mainly of a monohydric alcohol, a penetration enhancer and a polymer (which can be a hydrophilic polymer, hydrophobic or a combination of both). This material, gel-like in consistency, would allow a rapid onset of anesthesia and the penetration of the active agent into the skin.

The published American application US 2010/0092546A1 discloses compositions and methods for the treatment of chronic wounds, also including diabetic ulcers. The material would allow the transdermal administration of an agent that increases the activity of HIF-1 modulator to the wound, such as deferoxamine, deferiprone, deferasirox, etc. The topical dosage forms, which contain the lotion, would modulate agents and biodegradable gel ethylcellulose, and polyvinylpyrrolidone, and transdermal patches.

Also among the documents that report the use of shapes with adhesive properties, EP 649650B1 relates to a bioadhesive pharmaceutical composition in tablet form for controlled release of several local active principles through the buccal cavity, or systemically through a mucous membrane, but does not include topical anesthetics. Xanthan is a polymeric component of the composition mentioned.

In dental use, information is provided by the published American application US 2011/0315151 A1 regarding an adhesive molding for protection and relief of pain in the oral mucosa caused by orthodontic appliances. The compound can be made from orthodontic wax, polymers or other flexible biocompatible materials in the main form of strips. They can be applied directly to the braces to protect the lining of direct contact. The product can have different colors, flavors and display different topical anesthetics or drugs in their composition.

The use of biodegradable polymers as a matrix for controlled release of anesthetic is described in the International Publication WO 9936071 A1, which provides the use of a controlled release system consisting of 30 to 99.0% of a biodegradable polymer matrix, comprising biodegradable polymers such as albumin, collagen and polycaprolactone and polyalkylcyanoacrylates, non-biodegradable, among others, but does not include xanthan-containing embedded anesthetics.

The publication EP 1,132,080 also provides the use of a biodegradable polymeric matrix for incorporation of local anesthetics to control the persistent pain of various etiologies.

Meanwhile, the use of biodegradable microspheres is disclosed in the U.S. Pat. No. 6,214,387. The microspheres would be formed by a biodegradable polymer. Among the possible ones are the polyanhydrides, PLGA-poly (lactic acid-co-glycolic acid)—and polyorthoesters containing a catalyst, but no xanthan. Prolonged release of the anesthetic would be obtained by incorporating a glucocorticoid within the polymer matrix, or by co-administration with glucocorticoid microspheres. The type of anesthetic and the quantity would be selected based on the known pharmaceutical properties of different compounds.

Finally, the anesthetic efficiency and stability of topical anesthetic drugs in pharmaceutical preparations are closely related to the pH of the preparation. The relative proportion of the free base and the charged soluble or water-soluble cationic form of topical anesthetic affects the absorption and activity and depends on the solution pH. The water-soluble and fat-soluble balance should be carefully observed according to the place of use of the adhesive, as the tissues have pH variables; in the mouth, for example, the pH varies between 6.8 and 7.4, which causes the free base to be released and this enters the nerve that is rich in lipids.

The published application US 2008/0242731 A1 comprises the liquefied topical anesthetic formulations, its uses and methods for their preparations. It particularly refers to a combination of anesthetic substances, solubilizing agents, and viscosifying agents, resulting in a buffered topical anesthetic composition that has a pH, viscosity, and properties suitable for the reduction of pain associated with injury, trauma or any other source of pain sensitivity. Xanthan is among the cited viscosifying agents.

Xanthan is a non-toxic water-soluble fiber of microbial origin, produced by bacteria of the genus *Xanthomonas*.

Xanthan is released by the Ministry of Health as a food additive in Brazil since 1965 and by the FDA since 1969 and is currently widely used in pharmaceuticals.

The xanthan gum produced by *Xanthomonas arboricola* pv. *pruni* is a biopolymer that allows more progress in the field of development of new formulations of topical anesthetics adhesives, differentiated by their chemical composition and, in some cases, molar mass and high thermal resistance.

Various mechanical and dissolution properties may be obtained by using different xanthans, chemically modified or not, or by association with specific substances that allow the use of different methods for obtaining anesthetics adhesives.

Although xanthan is an extracellular biopolymer already established, it continues to demand research worldwide both in prospecting for new pathovars and producing strains and in search of xanthan with different features for new applications.

Research has been carried out in Brazil since the 80s and still, today, it is generating several patents and publications on xanthan production, including: BR8805325B1, BR406309-0 and WO 2006047845, BR0701765-0A2; BR1004194-0 and all documents cited on the use of *X. campestris* pv. *campestris*, except BR 8805325 B1 using *X. campestris* pv. manhiotis, and published application WO 2006047845A1 BR0406309-0 and *Xanthomonas arboricola* pv. using *pruni*, other species for the production of xanthan.

International Publication WO 2006047845A1 still stands out as the only document that has a different composition of the xanthan presence of rhamnose among its monomeric sugars, the *pruni* xanthan. This difference and the chemical modifications that can be made in their structure can profoundly transform the polymer and therefore its characteristics, enabling its use in various fields, bringing a new range of uses. To certify the safety of *pruni* Xanthan, various studies and tests were conducted that showed the absence of genotoxic and cytotoxic effects.

The chemical and physical properties of xanthan, especially the viscosity and stability with respect to pH variations, ion concentration, and temperature, make this polymer widely used in pharmaceutical, food, exploitation of oil, and as a thickener and stabilizing suspensions and emulsions.

Among the above-mentioned characteristics that stand out for the functionality of the proposed use in the said international document are the viscosity and pH stability over a wide range that is maintained almost unchanged from pH 2 to pH 12, which covers all dissociation constants (pK) of topical anesthetics or sites most commonly used mepivacaine 7.6; lidocaine and prilocaine 7.9; bupivacaine 8:1; 8.5 tetracaine and procaine 9:1.

A good anesthetic agent should have a low systemic toxicity, not be irritating to the tissues and not cause permanent damage to the nervous structures. The time for onset of local anesthesia should be as short as possible and the duration of action is sufficient for the surgical procedure, with reversible action.

Recent research is looking for ways to control the release of drugs to ensure an increase in the duration of the effect(s) of anesthetic(s) that are associated with decreased toxicity. Among these forms to obtain topical anesthetic formulations using carriers different in solubility and release of the anesthetic drug, but with high biocompatibility (with the oral mucosa) have been the specific focus of studies leading to the present application.

The use of polymers or biopolymers materials that allow the controlled release (such as xanthan with or without other biopolymers) and knowledge of the primary active ingredient (in this case the anesthetic) are fundamental to the development of new compositions. This will allow obtaining new pharmaceutical forms of topical anesthetics for the mouth and upper digestive tract, including the esophagus, such as wires, tapes, strips and adhesive films.

The possibility of using previous and exact doses depending on the applied area, the adhesiveness of the product in question, containing the anesthetic and added or not to drugs with other actions, which have their controlled release at the mucosal surface, will minimize or eliminate the occurrence of overdose and unwanted action in adjacent areas and prolong the effect of analgesia, which is short on topical anesthetics available today.

It would be interesting if the technique could have stickers, BAT type film or tape, consisting of biocompatible and biodegradable biopolymer matrix where the main constituent of support or matrix, which are incorporated in local anesthetics for topical use, is xanthan.

SUMMARY OF THE INVENTION

Broadly, the filmogenic compositions of the invention for the preparation of bioadhesives (BATs) for the controlled release of active principles for topical application to the outside or inside of the mouth or through a mucous membrane comprise the following:

A. A dry portion, comprising:

a) a polymer matrix selected from pure or mixed varieties of xanthan in any proportion, forming the support or polymeric matrix at concentrations of 1.0 to 95%, preferably 5.0% to 70.0% and more preferably 15 to 60%, and the matrix being combined with;

b) nanofiller type silicates or sheet silicates, natural or modified by organic ions or not, and silicas (including hydrophobic fumed silica), mixed or not, from 0.0% to 6.0%, preferably 0.01% to 5.0%; among the permitted food selected from Cloisite 30B, Cloisite Na;

c) nanofibers, combined or not, from 0.0% to 6.0%, preferably 0.1% to 5.0%, more preferably from 0.01% to 5.0%, selected from those obtained fibers from natural sources such as rice husks, rice straw, soybean hulls and sugarcane bagasse;

d) other natural polymers chemically modified or unmodified or semi-synthetic, selected from galactomannans, pectins, cyclodextrins, water-soluble modified celluloses, chitosan, saccharide polymers of microbial origin such as dextran and gellan, combined or not, 0.0% to 70.0% preferably from 0.0 to 60.0% and more preferably 0.0 to 50.0%;

e) additives in solid form selected from among food or pharmaceutical grade artificial coloring, or food or pharmaceutical grade inorganic pigments (qsp);

f) sweeteners include natural glycyrrhizin, neotame and stevioside and artificial sucralose, saccharin, cyclamic acid and its salts and acesulfame potassium (qsp);

g) flavoring, including powdered spices like cloves, cinnamon, nutmeg, ginger and cardamom, and natural-like flavoring substances such as vanillin, or artificial from food or pharmaceutical grade (qsp); and h) anti-caking agents, including tricalcium phosphate, calcium carbonate or magnesium and silicon dioxide, in sufficient amounts to achieve the desired effect (qsp) and complying with the specific regulations, if any;

B. A wet portion, comprising:

a) Wetting and dispersing the biopolymer matrix, combined or not, selected from:
  i) lipophilic, comprising edible oils and liquid lipids, food or not, including vegetable oils of rice, soybean, sunflower, canola, peanut and corn, coconut, nuts, almonds and edible nuts, copaiba, grape seed; and
  ii) hydrophilic comprising the synthetic dispersants and humectants including propylene glycol and polyethylene glycol, and natural sources, glycerin, glycerol, sorbitol and other polyols of similar effect, either pure or combined at 0.1% to 85.0% preferably from 0.5% to 65.0%, more preferably from 2.0% to 60.0%;

b) antifoams combined or not, selected from edible vegetable oils, such as those mentioned in item a, sub-item i, and emulsifiers of a very low nutritional or pharmaceutical grade (less than 3) Hydrolipophilic book value (BHL) as sorbitan trioleate (Span 85) and sorbitan tristearate (Span 65), from 0.0% to 5.0%, preferably from 0.5% to 3.0%, more preferably from 0.5% to 2.0%;

c) emulsifiers, food-grade or pharmaceutical, selected from among esterified mono and diglycerides, sorbitan esters such as Spans 60 and 80, polyoxyethylene esters such as WYRJ 45, Atlas 2142 and ATLAS 2127, polyoxyethylene sorbitan esters, such as Tweens 60 and 80, and lecithins, more specifically from 0.0% to 5.0%, preferably from 0.0% to 3.0%, more preferably from 0.0% to 2.0%;

d) antioxidants, combined or not, selected among primary and chelators, synergists such as butylated hydroxytoluene (BHT) and butylated hydroxyanisole (BHA), and ascorbic acid and erythorbic acid and their salts, respectively, suitably diluted 0.0% to 10% of the lipid fraction, preferably from 0.2% to 5%, more preferably from 0.5 to 1.5%;

e) food grade natural flavoring, combined or not, selected from essential oils, liquid or suitably diluted synthetic, preferably identical to natural, in amounts according to good manufacturing practices;

f) natural liquid sweeteners, selected from xylitol, erythritol, and other polyols (qsp);

g) organic dyes in solution; natural, such as chlorophylls, carotenoids, betalains, anthocyanins and carminic acid, or artificial ones, of food or pharmaceutical grade, in sufficient amounts to achieve the desired effect (qsp) and in compliance with specific regulations, if any;

h) acidity regulators or alkalizing agents, liquid or in solution, selected from inorganic bases and/or pharmaceutically acceptable low molecular weight amine bases, selected from sodium hydroxide and/or triethanolamine, for the composition of the pH adjustment in the range of 4, 5 to 9, and more preferably from 6.0 to 7.5;

i) preservatives, alone or in combination, suitably diluted, selected from methyl and ethyl paraben, sorbic acid and sodium or potassium sorbate; preferably from 0.1% to 2.0%, more preferably from 0.3 to 1.5% by weight relative to the total composition;

j) at least one local anesthetic, suitably diluted when solid, selected from benzocaine, tetracaine, procaine, lidocaine, ropivacaine, bupivacaine, prilocaine and articaine, alone in combination, at concentrations of 0.1% to 50% by weight of the total composition;

k) antimicrobial, anti-inflammatory, wound healing, cytotoxic or anti-tumor substances topically used, liquid or suitably diluted, in pharmacologically active concentrations (qsp); and where the percentage of the constituents of the dry portion (ps/pt) and wet portion (pu/pt) is calculated on the total weight of the components of the composition except for water or other solvents or solvent mixtures capable of solubilizing xanthan or solid pharmaceuticals.

The filmogenic compositions of the invention are processed by using known methods for producing bioadhesive films called BATs (Bioadhesives Anesthetics Topics).

The BATs have the following properties in matters such as cytotoxicity, anaesthetic effect and adhesion respectively.

Cytotoxicity was comparable to a commercial topical anesthetic 20% (20% Benzotop, DFL, Brazil) as specified in ISO 10995-5 (2009).

With respect to adhesion, the values for bond strength according to an adapted test to evaluate adhesion to dentures were comparable to materials like Corega paste and Corega powder; being lower than the values for Corega Strips group. The test used allows us to infer that the bioadhesive tested has adhesive characteristics in the simulated oral environment. The action of anesthetics occurs on rapid onset of action (15 seconds on average and fully anesthetized in three minutes) and acceptable taste. The advantage is not having adverse reactions Thus, the present invention provides filmogenic compositions for the preparation of bioadhesive BAT where a polymeric matrix of xanthan base is added in dry and wet components including at least one local anesthetic; the said components being processed by known methods to obtain a BAT.

The present invention also provides BATs in the form of a film with very low cytotoxicity and provided with adequate adhesion for use in medical, dental, and pharmaceutical applications.

The present invention further provides anesthetics with biofilms threads, bi- or multilayer, comprising at least an outer layer free of drugs so that at least one outer layer or an additional film is functioning as an auxiliary to reduce the patient's discomfort caused by the unwanted dissolution of drugs to adjacent areas.

BRIEF DESCRIPTION OF DRAWINGS

The FIGS. 2A and 2B show adhesive films with various extensions, thicknesses, and shapes.

DETAILED DESCRIPTION OF THE INVENTION

One aspect of the invention is the filmogenic composition for the controlled release of active ingredients, based on xanthan, was useful for the preparation of topical anesthetics adhesive.

Another aspect of the invention is the mono, bi or multilayer topical anesthetic adhesives obtained after processing the compositions of the invention.

Yet another aspect of the invention involves the use of the adhesives obtained according to the invention.

Advantageously, the adhesives of the invention exhibit effective adhesion, the area of application control and numbed region due to the use of a film, dosage control, water solubility control as well as the encapsulation of the unpleasant flavors of certain anesthetics or other drugs added together.

The filmogenic compositions for the controlled release of active ingredients according to the invention have a biomatrix or biopolymer matrix and structural polymer xanthan, biodegradable biomolecule and is biocompatible with the skin of the lips and oral mucous membranes and upper digestive tract. Potential fields of application of the anesthetic adhesives are proposed herein.

Xanthan, preferably used to make a pure or majorly form the support or biopolymer matrix with a structural and drug release function, must be produced by *Xanthomonas arboricola* pv. *pruni* called xanthan *pruni*, with purity suitable for use in pharmaceuticals and foods, high viscosifying power as measured by viscosity values of 1500 to 1700 mPas$^1$ or from 1200 to 1600 mPas$^1$ and low acetylation (preferably from 0.2 to 4% and more preferably 0.2 to 10%) while pyruvatation can be about 0.4 to 1.3%, from 2.5 to 3.0% or even from 4.0 to 4.8% (higher levels promote higher viscosity), chemically modified or not.

Still useful for the invention, pure or in combination, are other varieties of pharmaceutical and food grade xanthan having equivalent properties such as high heat resistance and rheological stability of the solutions against a wide range of temperature, pH, and ionic strength.

The matrix may also comprise other biopolymers with structural function, such as modified starches and starches, or to help control the release of anesthetic drugs and other drugs in the composition, preferably galactomannans, of microbial or non-microbial origin, such as guar gum, or other soluble biopolymers such as those from chemical modification of cellulose, namely methyl cellulose and the like, or water soluble, under specific conditions, such as chitosan, and various additives.

The polymer matrix may also be produced in combination with other hydrophilic and/or lipophilic components, such as food grade additives or pharmaceutical additives, in accordance with good pharmaceutical practice, including the Brazilian Pharmacopoeia and/or internationally acceptable manuscripts, such as USP.

Advantageously, xanthan is compatible with various existing anesthetics, both the amino group and the ester group or the amide group, which enables a multitude of anesthetics or associations of the same product.

Xanthan may be associated with many drugs, additives, and substances, which allows the obtaining of a variety of topical anesthetic adhesives, with different degrees of adhesion, dissolvability, flexibility, among others.

The filmogenic compositions of the invention for controlled release of active ingredients comprise dry components and wet components that are combined and processed in adhesive films of various types for the desired applications.

The dry components comprise the polymeric matrix selected from xanthan, combined or not, pure or compounding the polymeric matrix or carrier at concentrations of 1.0 to 95%, preferably 5.0% to 70.0% and most preferably 15 to 60%, the said matrix being combined with:

Nanofiller type silicates or sheet silicates, natural or modified by organic ions or non-organic ions, and silicas (including hydrophobic fumed silica), mixed or not, from 0.0% to 8.0%, preferably 0.01% to 6.0%, more preferably 0.1% to 5.0%.

Nanofibers, combined or not, from 0.0% to 6.0%, preferably from 0.1% to 5% more preferably from 0.01% to 5.0% selected from celluloses obtained from natural sources such as rice husks, wheat straw, soybean hulls and other permitted food.

Other natural polymers, chemically modified or unmodified or derived from semi-synthesis, selected from galactomannans, pectins, saccharide polymers of microbial origin such as gellan and dextran, combined cyclodextrins or not, or chitin and chitosan, and natural celluloses or modified in a proportion of 0.0% to 70.0%, preferably 0.0 to 60.0% and more preferably 0.0 to 50.0%.

Additives in a solid form selected from preservatives, colorants, sweeteners, flavorings, anti-caking agents, in amounts sufficient to achieve the desired effect (qsp).

The components of the wet portion comprise:

Wetting and dispersing agents of the biopolymer matrix, combined or not, selected from among: i) Lipophilic, comprising oils from natural sources, including vegetable oils of rice, soybean, sunflower, canola, peanuts and corn, coconut, nuts, almonds and edible nuts, copaiba, of grape seed and phospholipids such as lecithins; and ii) Hydrophilic, comprising the synthetic dispersants and humectants including propylene glycol and polyethylene glycol, and those of natural sources, glycerin, glycerol, sorbitol and similar effect polyols, alone or combined, from 0.1% to 85.0%, preferably from 0.5% to 65.0%, more preferably from 2.0% to 60.0%;

Defoamers, combined or not, selected from among those allowed for food or allowed for drugs, selected from sorbitan trioleate (Span 85) and sorbitan tristearate (Span 65), 0.0% to 5.0%, preferably 0.5% to 3.0%, more preferably from 0.5% to 2.0%;

Emulgents, selected from among mono- and esterified glycerides, sorbitan esters, such as Spans 60 and 80, polyoxyethylene esters, selected from WYRJ 45, Atlas 2142 and Atlas 2127 esters of polyoxyethylene sorbitan, selected from Tweens 60 and 80 and lecithin, 0.0% to 5.0%, preferably 0.0% to 3.0%, more preferably from 0.0% to 2.0%;

Antioxidants, combined or not, selected among primary and chelators, synergists such as butylated hydroxytoluene (BHT) and butylated hydroxyanisole (BHA), and ascorbic acid and erythorbic and their salts, respectively, suitably diluted, 0.0% to 10% of the lipid fraction, preferably from 0.2% to 5%, more preferably from 0.5 to 1.5%;

Natural flavors, combined or not, selected from essential oils, or synthetic, preferably identical to natural, in amounts according to good manufacturing practices (qsp);

Dyes and pigments for drugs and food, selected from dyes and natural organic pigments, chlorophylls, carotenoids, betalains, and anthocyanins, or inorganic such as titanium dioxide, calcium carbonate, iron oxides in amounts sufficient to obtain the desired effect (qsp);

Acidity regulators or alkalizing agents selected from inorganic bases and/or low molecular weight pharmaceutically acceptable amines, selected from sodium hydroxide and/or triethanolamine for the composition of the pH adjustment in the range 4.5 to 9 and more preferably from 6.0 to 7.5; and:

At least one local anesthetic selected from benzocaine, tetracaine, procaine, lidocaine, ropivacaine, bupivacaine, articaine, prilocaine and in concentrations by weight from 0.1% to 50%, preferably 2.0 to 45.0%, more preferably 3.0 to 40.0% by weight.

Compounds with antimicrobial, anti-inflammatory, wound healing, cytotoxic or anti-tumor characteristics of topical use in pharmacologically active concentrations (qsp); and where the percentage of the constituents of the dry portion (ps/pt) and wet portion (pu/pt) is calculated based on the total weight of the components of the composition except for water or other solvents or solvent mixtures capable of solubilizing xanthan or other solid drugs.

For illustrative purposes, Table 1 below summarizes the percentages by weight of components of the inventive compositions.

TABLE 1

| Components | Range in % | | |
|---|---|---|---|
| | Wide range | Medium range | Short range |
| Xanthan | 1-95 | 5-70 | 15-60 |
| Water soluble polymer | 0.0-70 | 0-60 | 0-50 |
| Nanofillers | 0-6 | 0.1-0.5 | 0.15-5 |
| Nanofibers | 0-6 | 0.1-0.5 | 0.15-5 |
| Plasticizers | 0.1-85 | 0.5-65 | 5.0-60 |
| Dispersants | 0.1-85 | 0.5-65 | 2.0-60 |
| Defoamers | 0-5 | 0.5-3 | 0.5-2.0 |
| Emulsifiers | 0-5 | 0-3 | 0-2 |
| Antioxidants | 0-10 | 0.2-5 | 0.5-1.5 |
| Preservatives | 0.1-2.0 | 0.2-1.8 | 0.3-1.5 |
| Anesthetics | 0.1-60 | 3-45 | 5-40 |

TABLE 1-continued

| Components | Range in % | | |
|---|---|---|---|
| | Wide range | Medium range | Short range |
| Acidity Regulators for pH between 4.5 and 9.0 | qsp | qsp | qsp |
| Antimicrobial, anti-inflammatory, healing | qsp | qsp | qsp |
| Sweeteners, colors | qsp | qsp | qsp |

Table 2 below lists some bioadhesive formulations of the invention prepared for cell toxicity tests.

TABLE 2

| COMPONENTS | EXAMPLES | | | |
|---|---|---|---|---|
| | 1 | 2 | 3 | 4 |
| Xanthan (g) | 3 | 3 | 3 | 3 |
| Cloisite 30B (g) | 0.15 | 0.15 | — | 0.15 |
| Ca triphosphate (g) | 0.03 | — | 0.05 | — |
| Glycerin (g) | 2.9 | 3.0 | 3.0 | 3.0 |
| Tween (g) | 0.5 | 0.3 | 0.3 | 0.3 |
| Copaiba (g) | 0.1 | 0.3 | 0.3 | 0.3 |
| Benzocaine (g) | 1.0 | 1.7 | 0.85 | — |
| Methylparaben (g) | 0.07 | — | 0.06 | — |
| Ethylparaben (g) | 0.01 | — | 0.02 | — |
| Water + alcohol (ml) | 260 | 300 | 300 | 250 |
| Characteristics | Very dry, low adhesive properties | Medium adhesive properties. | Medium adhesive properties. More flexible than example 2. | Dry. Medium adhesive properties. Flexible and translucent |

The cytotoxicity of the products of the invention is evaluated with the cell line of mouse fibroblasts (NIH/3T3).

The test is performed according to ISO 10993 (2009). The cell suspension is plated at a concentration of $2 \times 10^4$ cells per well and delivered into a cell culture dish of 96 wells. Each well receives 200 µl DMEM (Dulbecco's Modified Eagle Medium) supplemented with 10% Fetal Bovine Serum. The plate is then incubated at 37° C. in an atmosphere containing 5% $CO_2$ for 24 hours. The groups used are shown in Table 1. In control wells, 200 µl DMEM (Dulbecco's Modified Eagle Medium) is supplemented with fetal bovine serum 10%. After removal of the test extracts, 200 µl PBS (phosphate buffered saline) and 20 µl of MTT (tetrazolium salt [3-(4,5-dimetltiazol-2-yl)-2,5-diphenyltetrazolium bromide] are added to each well. The plate is incubated in a room without light for 24 hours at 37° C. After that, MTT is aspirated and 200 µl dimethylsulfoxide (DMSO) is added to each well. Thereafter, absorbance at 540 nm is measured using a spectrophotometer and the results were analyzed statistically.

The data are tabulated and submitted to Kruskal-Wallis nonparametric statistical analysis and Tukey's complementary test ($p < 0.05$). In the analysis, the product of the invention M20, prepared according to Example 2 of Table 2 above, with 20% benzocaine, demonstrated statistically similar results to the commercial control (Benzotop, DFL, Brazil).

Figure 10:
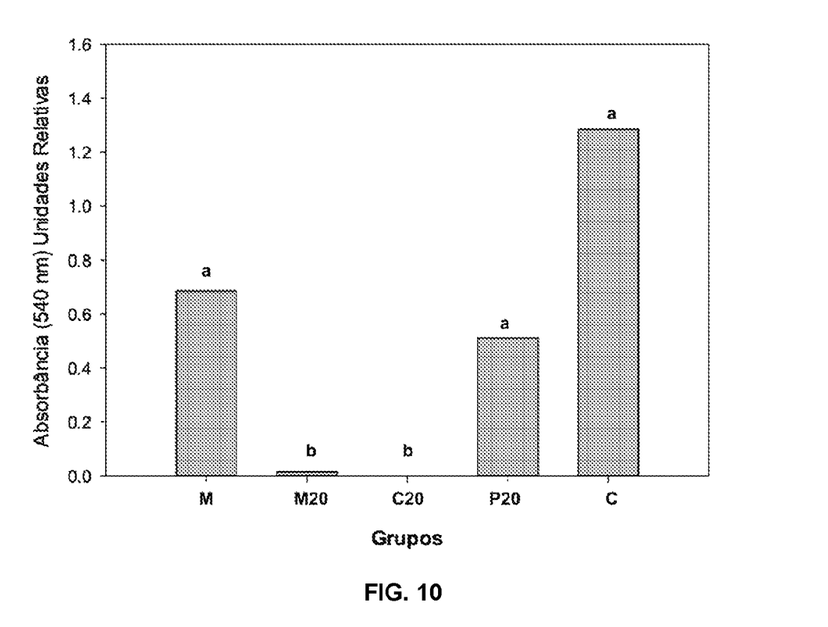
FIG. 10 attached is a bar graph for graphical illustration of the statistical analysis between groups of anesthetics in the NIH/3T3 fibroblast cell line cytotoxicity test (Absorbance at 540 mm), where different letters indicate a statistically significant difference between groups ($p<0.05$).

The results of cytotoxicity testing are illustrated in FIG. 10. In FIG. 10, the legend is used as shown in Table 3 below.

As an illustration, the same results are given in Table 3 as the numerical results of the cytotoxicity tests.

TABLE 3

| GROUP | DESCRIPTION | ABSORBANCE (540 nm)* |
|---|---|---|
| M | Negative control of bioadhesive | 0.686 (±0.186)$^A$ |
| M20 | Product of the invention with 20% benzocaine | 0.015 (±0.027)$^B$ |
| C20 | Commercial topical anesthetic 20% (Benzotop 20%, DFL, Brazil) | 0.000 (±0.000)$^B$ |
| P20 | 20% benzocaine powder | 0.511 (±0.032)$^A$ |
| C | Cell control (Positive controle) | 1.284 (±0.039)$^A$ |

The negative control means membrane without the anesthetic; Positive control means only the cells that were cultured in the wells, without contact with any material.
*Different letters indicate statistically different groups ($p < 0.05$).

After defining the composition of the formulation, the method of production is chosen.

Solvents and/or diluents are required to allow the formation of the matrix and the incorporation of the primary active ingredient, namely the topical anesthetic, or other solid drugs in the matrix.

The solvents or diluents used are preferably water for xanthan and other water soluble polymers and amine type drugs, and alcohol and weak acid solutions as required.

For some water soluble drugs such as local anesthetics of the ester type, edible vegetable oils may be used such as canola and rice; or of pharmaceutical use, such as grape seed and almonds, or essential oils with properties that are sapid, odorants and even pharmacological, such as clove oil, cinnamon, ginger, mint and other such diluents; one or several of these but not limited thereto.

Anesthetics in liquid form can be inserted into the hydrophilic and/or lipophilic portion of the matrix for adhesive construction.

All mixtures and additions must be made respecting and avoiding possible incompatibilities between the components, making use of emulsifiers as needed. These different formulations or bioadhesive compositions allow obtaining a multitude of different characteristics as to their physical, chemical and physicochemical properties, which allows for the different uses.

The casting method (solvent evaporation method) is the preferred method for the preparation of the bioadhesive invention.

Other methods include extrusion or even other methods of producing tapes, wires, strips and adhesive films, known or that may be used for this type of production, provided that they do not adversely modify the properties of the anesthetics and other added drugs or with the same properties of the composition.

The obtainment of the finished bioadhesive threads by casting method provides ways of bioplastic or adhesive biofilm forms that can be modeled in different formats at the end of the process, enabling several applications of the topical bioadhesive.

The preparation of the biopolymer compositions and the preparation of adhesives may be performed in a single step or in two or more steps, depending on the method used to obtain the product.

Production by the casting method, for example, is performed in two stages, the preparation stage of the composition followed by the preparation of the product based on solvent evaporation.

In the preparation by solubilization, xanthan, and other water-soluble or solubilizable polymers which will form the polymeric matrix, should be completely solubilized in water and/or alcohol solution of suitable pH.

To this solution, other constituents are added, if any, such as humectants, anti-caking agents, antifoams, preservatives, dyes and colorings, antioxidants, sweeteners, salts, and water-soluble drugs, fillers and/or nanofillers, or some of these, depending the end product desired, respecting and avoiding possible incompatibilities and making use of emulsifiers as needed.

The direct incorporation of these materials, or previously dispersed or solubilized or emulsified or mixed, as to its characteristics, without loss of homogeneity of the composition, namely, uniform distribution of the components is possible because the xanthan solution has high stabilizing capability of suspensions and emulsions.

After mixing the constituents of the biopolymer matrix composition for the processing and obtaining the adhesive threads by the casting method, it is still necessary to add specific conditions for solvent evaporation, with the use of heat being preferred.

Other forms for partial removal of the solvent may be used until complete removal of the solvent, and other volatilizable components is complete so that the formation of the topical film, tape or strip occurs.

This method enables the shaping or embossing of adhesives that can easily be made at the end of the formation step of the adhesive.

Furthermore, the casting method makes it possible to obtain special multilayer films by the addition of liquid compositions of a different formulation, for example, without anesthetic, on previously formed anesthetic film; the second added layer should also have the solvent evaporated for final formation of the bilayer adhesive.

The extrusion method may be used provided that the extrusion conditions do not alter the properties of topical anesthetics and other drugs in the composition.

When using this method to obtain compositions by solubilization, this will be followed by pre-concentration.

If the preparation is by liquid phase dispersion, the compositions should subsequently be subjected to temperatures below the melting point of the xanthan or combinations thereof.

In this process, obtaining combinations of the materials initially follows the same procedure, but the addition of the constituents is reset and/or solvent content used is not sufficient to completely solubilize the xanthan.

In the extrusion process, the final product is not in the form of biofilms adhesive; it is necessary to subject it to a further step for stamping the adhesive. To obtain the adhesives, it is necessary for the extrusion of the material to pass by a new melting, now outside the extruder, wherein the molding step can be done by thermoforming.

Topical anesthetics adhesives of the invention are tested for their retention and adhesion using standard tests.

The adhesives are prepared by casting or by extrusion.

In principle, topical anesthetics do not have adhesive properties, since the usual presentation is a gel/paste and liquid (spray), so there is no study reporting adhesiveness thereof. Thus, the adhesion test was based on articles for denture fasteners, which has the most similar presentation with the adhesive product of the invention. As there is no ISO standard for such fasteners, the evaluation was adapted from articles for this type of material.

The analysis of retention and stickiness or adhesion is carried out through the acrylic resin specimens mounted on mechanical testing machines to perform a tensile test. Marketed denture fixatives are used as reference materials for this test.

The groups (n=12) are shown in Table 4 below.

Acrylic resin cylinders are 21.9 mm in diameter and 55 mm in height with a flat surface where the materials are applied. Initially, 0.3 g of each tested material is applied on the polished surface of the lower cylinder attached to the machine base, and the resin cylinder previously immersed in artificial saliva. Then, the upper cylinder with the flat side facing downwards is positioned on the lower cylinder to leave the interposed material. A pressure of about 2 kg is applied to the upper cylinder acrylic resin (mobile) for 15 seconds to simulate the applied pressure of fasteners on an upper denture. The upper mobile cylinder is connected to the load cell, the tensile test is carried out with a speed of 1 mm/min until the separation of the rolls. The maximum adhesion strength (MPa) was recorded at the time of separation from the set.

The data were tabulated and submitted to Kruskal-Wallis nonparametric statistical analysis and Tukey's complementary ($p<0.05$). The product of the invention called M20, prepared in Example 2 of Table 2, demonstrates bond strength values similar to the Corega Adhesive Paste and Corega Powder being, however, lower than the Corega tape group.

From the test used, it can be inferred that the bioadhesive of the invention as tested possesses adhesive characteristics in a simulated oral environment.

Figure 11:
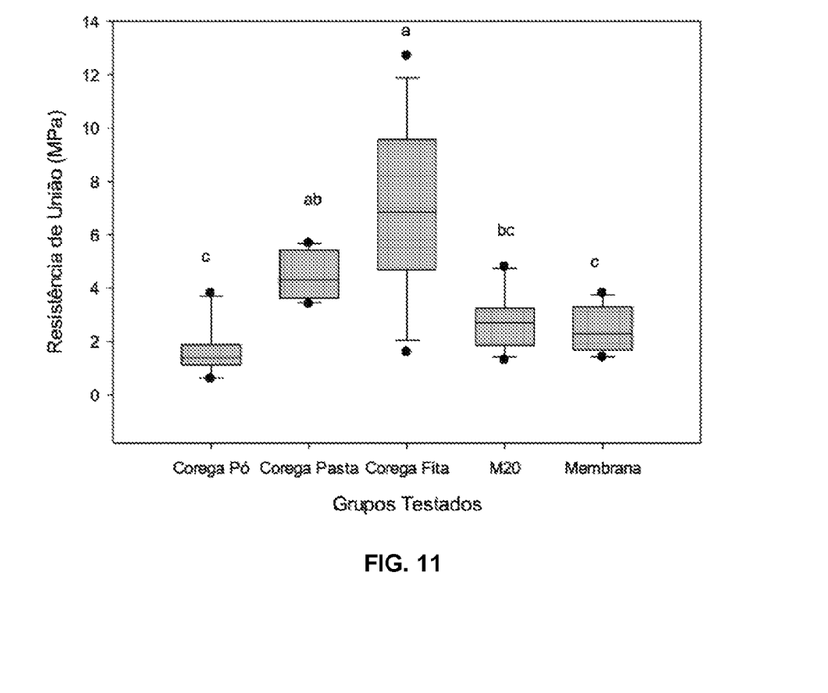
FIG. 11 is a graphical illustration attached via the adhesive Box plot analysis between groups of anesthetics when compared to denture fixatives. Different letters indicate a statistically significant difference between groups ($p<0.05$).

FIG. 11 attached illustrates the retention and adhesiveness test results. In this Figure, the following groups have the same interpretation as in Table 4 below. The bond strength data obtained for the various groups are expressed in MPa.

TABLE 4

| GROUPS | DESCRIPTION | BOND STRENGTH (MPa)* |
| --- | --- | --- |
| Corega Powder | Corega ® Powder | 1.708 (±0.994)$^C$ |
| Corega Paste | Corega ® Paste | 4.442 (±0.865)$^{AB}$ |
| Corega Strip | Corega ® Strip | 6.958 (±3.222)$^A$ |
| M20 | Product of the invention with 20% benzocaine | 2.816 (±1.077)$^{BC}$ |
| Membrane | Negative controlo of bioadhesive | 2.425 (±0.823)$^C$ |

All Corega ® products are owned by Glaxo Smith Kline, UK.
*Different letters indicate statistically different groups ($p < 0.05$).

As shown in Table 4 above, the item "negative control membrane" means a membrane free from the anesthetic.

The lack of adhesiveness of topical anesthetics of prior art is extremely problematic, especially in wet areas, which is solved by the characteristics of the adhesives currently proposed.

According to the invention, the material can be constructed although they do not have any prior adhesiveness, when the material comes into contact with a damp area, it is fixed and remains in place, releasing the anesthetic and other drugs from the composition, which facilitates the use in the oral cavity and upper digestive tract, including the esophagus.

In the oral cavity, this feature facilitates dental procedures and provides a more effective analgesia than traditional anesthetics, mainly presented in the form of mouthwashes, solutions, gels or ointments used for this purpose.

The adhesiveness of the material may be inherent or arise at the time of contact with moist areas, such as the oral mucosa. For areas that are not normally damp such as the lips, the adhesive can exhibit prior adhesiveness to facilitate attachment on the site. This adhesiveness guarantees the permanence of the material for the time required to start the dental procedure completely painless or with a significant minimization of this.

Regarding some topical adhesives and the invention's adherence, the results also showed high stickiness (tack) which, in addition to being advantageous for use in less humid places, is interesting for obtaining films, foil and bi- or multilayer strips.

Figure 2A:
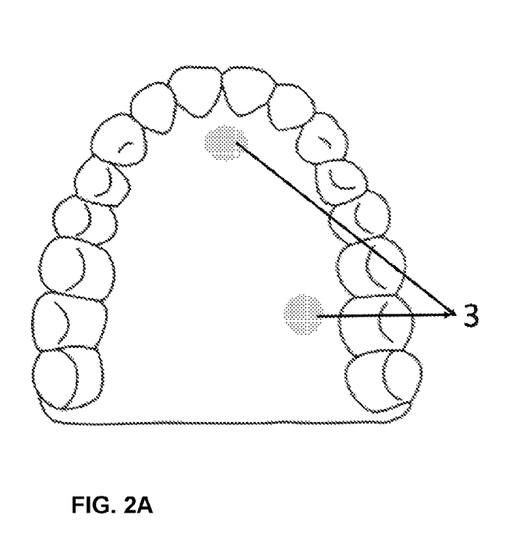
Figure 2B:
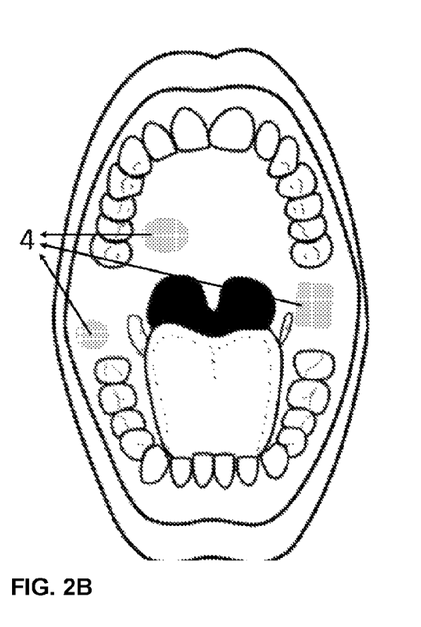

For the various adhesives developed for this application, different adhesion tests were performed on the oral mucosa, and outside, between the anesthetic adhesives, and between the adhesive and different materials in a qualitative manner, as can be seen in FIGS. 2A and 2B attached.

Thus, all the films, tapes and adhesive strips of topical anesthetics obtained by using different combinations of preliminary tests remained adhered to the oral mucosa for a period of 30 minutes to 3 hours.

The topical anesthetic adhesives of the invention, besides its effective adhesiveness, still have the advantage of limiting its anesthetic action to the applied area. This provides the safety of anesthetizing only the region in which the procedure will be performed, which does not occur with anesthetics presented in the form of mouthwashes, solutions, gels or ointments that do not allow this control action area, inducing gustatory anesthesia.

The anesthetics adhesives of the invention can even be designed so as to perfectly match areas with specific shapes, such as around the teeth, or even have markings that guide the exact place for punctures, as can be seen in the drawings in FIGS. 1 to 5. These adhesives with indicative markings are also applied in the medical field, in surgeries and procedures in the upper digestive tract.

The method of production and the composition of adhesives allow for pre-determining the concentration of anesthetics and other drugs added, depending on the area of adhesion and the onset of drug release so that perfect dose control is possible. Thus, they allow a more efficient control of the desired action, and provide a more effective analgesia in the oral mucosa with no toxic or allergenic effects caused by overdoses. The controlled release is made possible through the use of xanthan gum and of the auxiliary polymers which can be associated with it.

The topical anesthetic adhesive materials proposed herein may be soluble in water and have controlled solubility. This may vary from completely dissolvable and soluble, at higher or lower speed, to fully not soluble, suffering only waterlogging, which reduces the release rate of the drug and prolongs the anesthetic action.

Xanthans may have varying translucency and opacity and these characteristics are transferred to the adhesive threads. However, the concentration and type of substances having a pharmacological action, such as anesthetics and the like, or only technological, such as fillers and nanofillers that may be added, may alter the translucency of the adhesive; thus, the adhesives can range from translucent to opaque.

Furthermore, the biopolymer matrix used in the topical adhesives of the invention permits the addition of various dyes, making it possible to create adhesives with different colors.

The encapsulating action of the aromas and flavors of xanthan is well known. Thus, the particular composition of the biomatrix has the ability to encapsulate the unpleasant taste of some anesthetics and this provides a differentiating factor because it contributes to the masking of the undesirable taste of the anesthetic, which provides a lower rejection by the patient; thus, facilitating its use.

In addition, some studies have shown the capacity to potentiate the action of antioxidants. Thus, the bioadhesive matrix of anesthetics proposed here can preserve the drugs contained therein.

An additional means of controlling the release of drugs to adjacent areas that are part of the composition of anesthetics bioadhesive of the invention comprises, in addition to the bioadhesive layer containing the anesthetic and pharmaceuticals, the addition of at least one thin film or film/layer which does not contain anesthetic drugs or others to form the bi- or multilayers of the anesthetic bioadhesives, so that this additional layer(s) or film(s) acts as an aid to reduce the patient's discomfort caused by the unwanted dissolution to adjacent areas.

The outside(s) layer(s) is (are) consist(s) of insoluble or low dissolving plastic materials formed from the xanthan polymeric matrix, preferably xanthan *pruni* compositions in specific association, more preferably chemically modified, and/or by addition of other biocompatible and biodegradable materials such as thin films or post-formed films, PHAs low or medium crystallinity, including PHB of hydroxymethylpropylcellulose phthalate or copolymer of methacrylic acid/methacrylate methyl; or non-biodegradable and non-toxic non-edible films, such as food grade PVC.

The strategy of forming bi- or multilayer films as a means of reducing an undesired drug release to adjacent areas covered by the local anesthetic adhesives can be used for all of the adhesives object of the present application.

Advantageously, the present bioadhesives have the following characteristics:

anesthetize only the desired area with a reduction in the area of anesthetic activity, freeing the patient from receiving unnecessary doses of drugs contained in the adhesives, which makes them even safer;

greater penetration of anesthetic due to adhesiveness and stable viscosity that keeps the drug longer and in greater concentration at the site of action;

being wholly or partly water-soluble but always biocompatible with the tissues of areas of use, namely the mouth and upper digestive tract;

the dissolution time at the time of use may vary or even not dissolve while maintaining the release of the active principle of the anesthetic if necessary;

the matrix of the adhesives is edible and because they are biodegradable they do not require special disposal;

the matrix allows obtaining the AAT adhesives by different methods;

are of small volume, light and easy to be packaged, stored, transported and used; and in addition to anesthetizing, they can play other roles, such as protecting injured or ulcerated surfaces.

The description of the invention as well as the description of the accompanying figures, which are given as non-limiting examples will explain the invention well.

Figure 1:
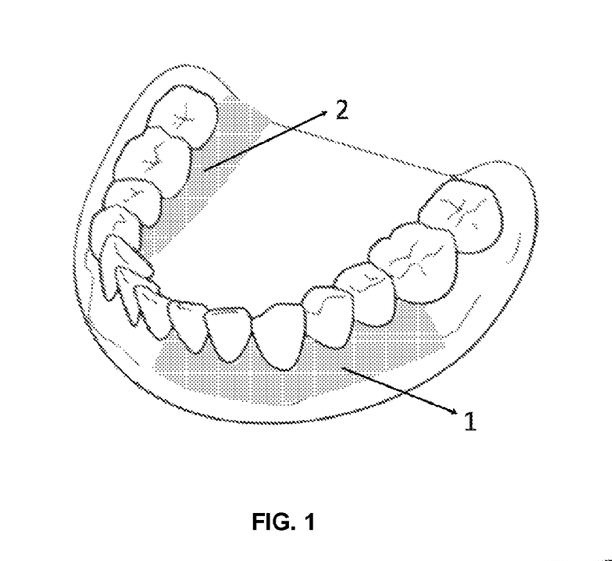
FIG. 1 attached depicts topical anesthetics adhesive films applied to the gingival mucosa and/or alveolar mucosa in the buccal (1) or lingual/buccal (2).

Initially, FIG. 1 represents anesthetic topical adhesive films applied to the gingival mucosa and/or alveolar mucosa on the buccal (1) or lingual/buccal (2) with anatomical extensions and contours for crowns of the upper and lower dental arches.

FIGS. 2A and 2B show adhesive films with various extensions, thicknesses, and shapes applied as a local anesthetic film in anatomical regions of the palatine mucosa prior to the infiltration of the anesthetic for local or regional blockade (3 and 4).

Figure 3:
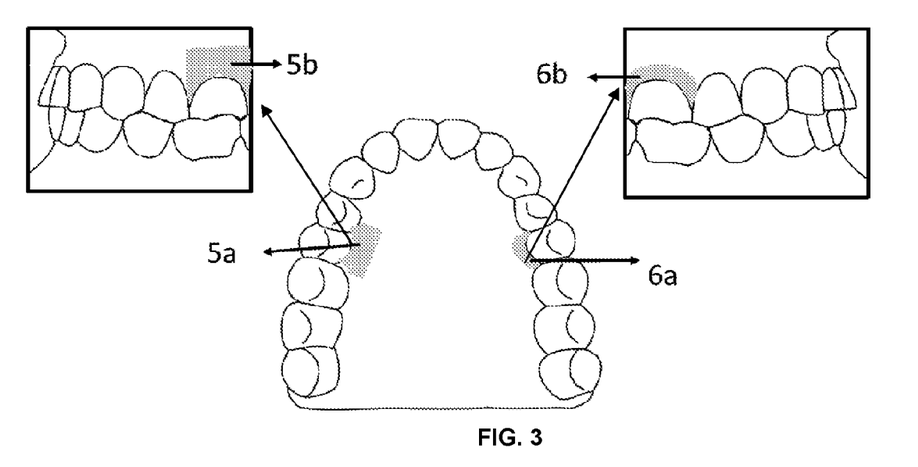
FIG. 3 represents anesthetic adhesive films with a full outline of topics or anatomical cervical part with 360° contour on a tooth that will receive a clamp for absolute isolation.

FIG. 3 shows the topical anesthetic adhesives, total or partial outline or full anatomical lap films with a 360° contour on a tooth that will receive a clamp for absolute isolation, protruding from the palatal/lingual regions (5a) to vestibular regions of the gums (5b); wire, tape or fibers intertwined for gingival protection (6a and 6b).

Figure 4:
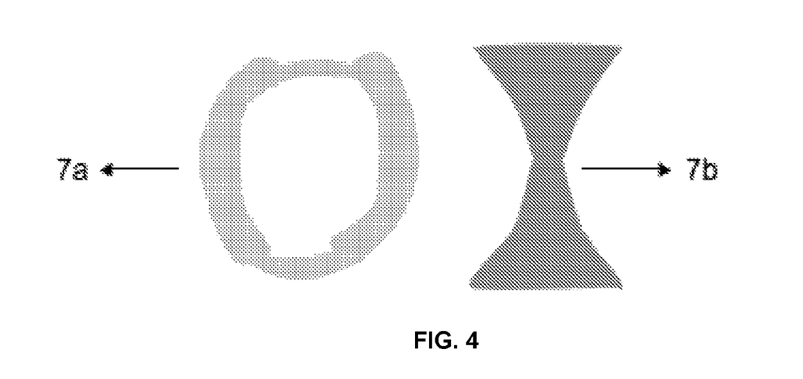
FIG. 4 attached illustrates anesthetic adhesive films with variants of anatomical conformation for insertion and positioning in interproximal areas.

FIG. 4 shows topical anesthetics adhesive films with variants of anatomical design for insertion and placement in interproximal regions and can be invaginated into the gingival sulcus (7a and 7b).

Figure 5:
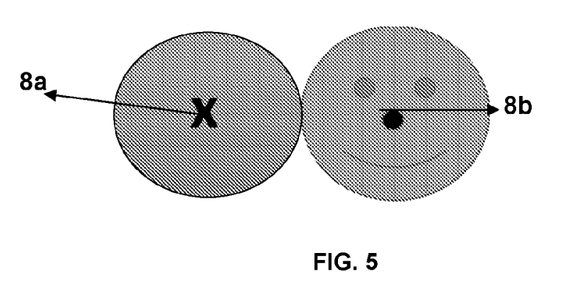
FIG. 5 illustrates attached adhesive films with topical anesthetic effect in various shapes and colors, and with centralized chromatic markings.

FIG. 5 represents adhesive films with topical anesthetic effect in various shapes and colors, and with centralized chromatic markings indicating the needle puncture site (8a and 8b) for anesthetic infiltration.

Figure 6A:
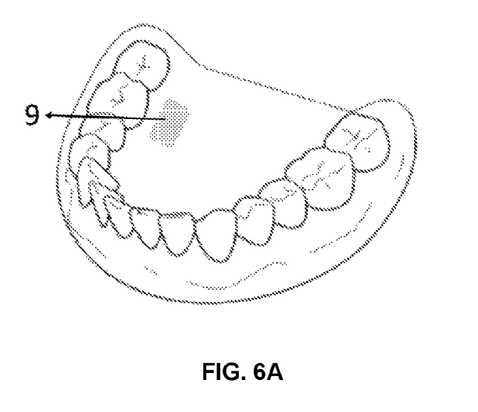
FIGS. 6A and B attached exemplifies the use of topical anesthetics films in ulcerated and/or traumatic injuries.
Figure 6B:
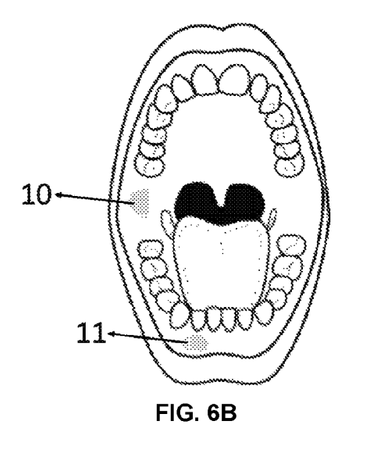

FIGS. 6A and B illustrate the use of topical anesthetics films in ulcerated and/or traumatic lesions in various regions of the oral mucosa (9, 10 and 11).

Figure 7:
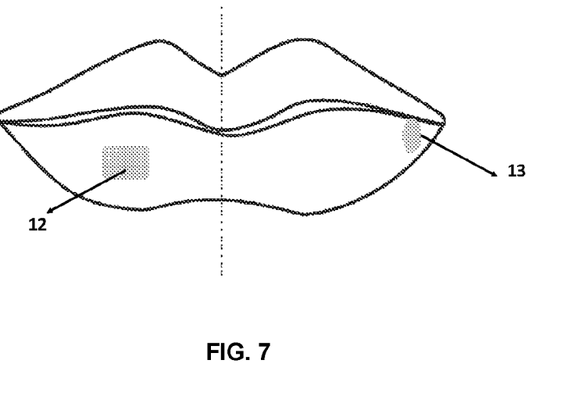
FIG. 7 attached shows anesthetic adhesive films threads for insertion and positioning on the lips.

FIG. 7 depicts topical anesthetics adhesive films with shaping variants (12, 13) for insertion and placement in the mouth.

Figure 8:
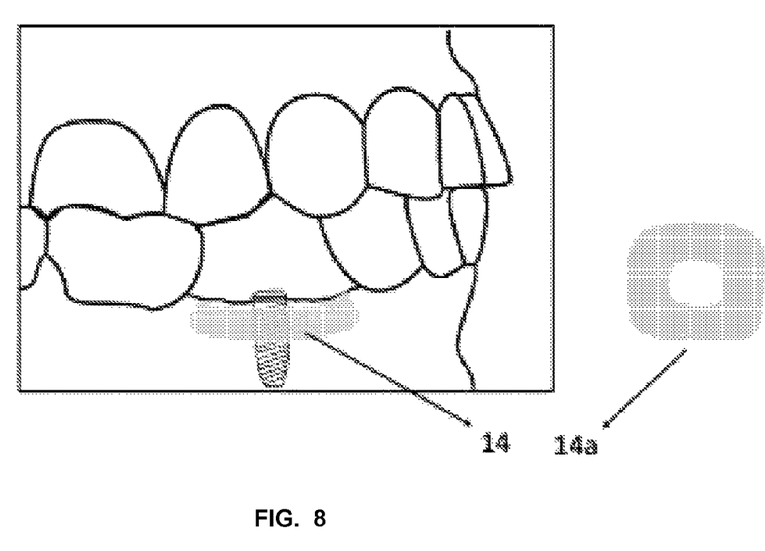
FIG. 8 attached shows adhesive film according to the invention inserted and positioned in a region adjacent to the dental implant.

FIG. 8 depicts adhesive film inserted and positioned in the region adjacent to the dental implant (14) showing the designed variant in detail (14a).

Figure 9:
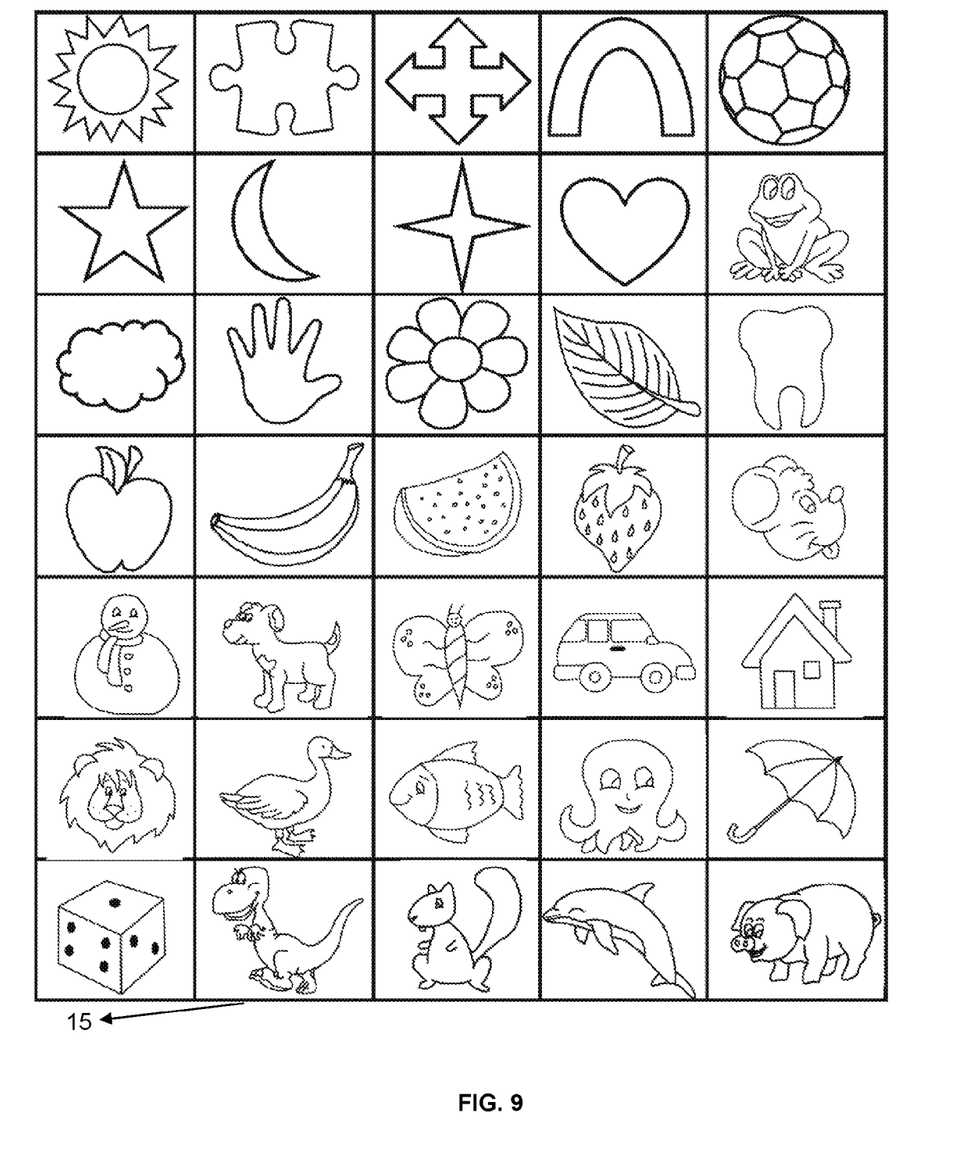
FIG. 9 attached exemplifies several shapes of the anesthetic adhesive films of the invention, with a playful appeal for children's use.

FIG. 9 illustrates various formats that can present the anesthetic adhesive films with playful appeal to be preferentially used by a child.

FIGS. 10 and 11 are detailed above in this report and relate respectively the results of cytotoxicity and retention and adhesion tests.

The invention claimed is:

1. A filmogenic composition for controlled release of topical anesthetics (TAB), said composition comprising:
   1) A dry portion, comprising:
      a) from 1% to 95% by weight of said dry portion of a biopolymer matrix of xanthan produced by *Xanthomonas arboricola* pathovar *pruni*, wherein the viscosity of 1% xanthan *pruni* in solution of said xanthan is from 1200 to 1700 mPas 1, the degree of acetylation is between 0.2% and 4.0% and the pyruvate degree is from 0.4% to 1.3%;
      b) from 0.0% to 6.0% by weight of said dry portion of nanofillers selected from the group consisting of silicates or sheet silicates, natural or modified by organic ions, pyrogenic silica and silicas, and combinations thereof;
      c) from 0.0% to 6.0% by weight of said dry portion of nanofibers selected from the group consisting of rice husks, rice straw, soybean hulls, sugarcane bagasse, and combinations thereof;
      d) from 0.0% to 70% by weight of said dry portion of other natural polymers chemically modified or unmodified or semi-synthetic, selected from the group consisting of starches, modified starches, galactomannans, pectins, cyclodextrins, water-soluble modified celluloses, chitosan, saccharide polymers of microbial origin, and combinations thereof; and
      e) up to 1.6% by weight relative to the weight of xanthan of an anti-caking agent;
   2) a wet portion, comprising:
      a) from 0.1% to 85.0% by weight of said wet portion of liquid dispersants/wetting agents, comprising i) lipophilic agents selected from the group consisting of edible oils and liquid lipids, vegetable oils of rice, soybean, sunflower, canola, peanut and corn, coconut, nuts, almonds and edible nuts, copaiba, and grape seed; and ii) hydrophilic agents selected from the group consisting of propylene glycol and polyethylene glycol, glycerin, glycerol, sorbitol, and combinations thereof;
b) from 0.0% to 5.0% by weight of said wet portion of antifoaming agents selected from the group consisting of edible vegetable oils, emulsifiers, and combinations thereof, said emulsifiers selected from the group consisting of sorbitan trioleate and sorbitan tristearate;
c) from 0.0% to 5.0% by weight of said wet portion of emulsifiers selected from the group consisting of esterified mono and diglycerides, sorbitan esters, polyoxyethylene esters, polyoxyethylene sorbitan esters, and lecithins;
d) from 0.0% to 10% by weight of said wet portion of antioxidants selected from the group consisting of primary antioxidants and chelators, synergists selected from the group consisting of butylated hydroxytoluene (BHT) and butylated hydroxyanisole (BHA), ascorbic acid and erythorbic acid and their salts, and combinations thereof;
e) acidity regulators or alkalizing agents, liquid or in solution, selected from the group consisting of inorganic bases and pharmaceutically acceptable low molecular weight amine bases, said amine bases selected from the group consisting of sodium hydroxide and triethanolamine, for pH adjustment in the range of 4.5 to 9;
f) from 0.1% to 2.0% by weight relative to total weight of said composition, of preservatives, alone or in combination, selected from the group consisting of methyl and ethyl paraben, sorbic acid, and sodium or potassium sorbate;
g) from 97% to 98% by weight relative to the total weight of the composition, of water and alcohol; and
h) from 0.1% to 50% by weight relative to the total weight of the composition of at least one topical, liquid or solubilized anesthetic, selected from the group consisting of benzocaine, tetracaine, procaine, lidocaine, ropivacaine, bupivacaine, prilocaine, articaine, and combinations thereof.

2. The filmogenic composition according to claim 1, wherein the anti-caking agent is tricalcium phosphate.

3. The filmogenic composition according to claim 1, wherein the topical anesthetic is used in combination with anti-microbial or anti-inflammatory agents.

4. The filmogenic composition according to claim 1, wherein the saccharide polymers of microbial origin are selected from the group consisting of dextran and gellan.

5. The filmogenic composition according to claim 1, wherein said composition is mixed and submitted to a continuous casting process to produce films, strips or tapes of topical anesthetic bioadhesives.

6. A topical anesthetic bioadhesive (TAB) for the controlled release of active principles, comprising a bioadhesive in the form of films, strips or tapes obtained from processing the composition according to claim 1.

7. The topical anesthetic bioadhesive (TAB) according to claim 6, wherein said bioadhesive comprises one single layer.

8. The topical anesthetic bioadhesive (TAB) according to claim 6, wherein said bioadhesive comprises an inner, anesthetic-containing layer and an anesthetic-free outer layer.

9. The bioadhesive according to claim 8, wherein said outer layer comprises a xanthan or a low or medium crystallinity polyhydroxyalkanoate (PHA), or hydroxymethylpropylcellulose phthalate.

10. The bioadhesive according to claim 9, wherein said outer layer xanthan is selected from the group consisting of xanthan gums produced by *Xanthomonas arboricola* pathovar *pruni*, *Xanthomonas campestris* pathovars *campestris* and manihotis, and combinations thereof.

11. The filmogenic composition according to claim 1, said composition comprising:
1) a dry portion, comprising:
a) from 5% to 70% by weight of said dry portion of a biopolymer matrix of xanthan produced by *Xanthomonas arboricola* pathovar *pruni*, wherein the viscosity of 1% xanthan *pruni* in solution of said xanthan is from 1200 to 1600 mPas1, the degree of acetylation is between 0.2% and 1.0% and the pyruvate degree is from 4.0% to 4.8%;
b) from 0.01% to 5.0% by weight of said dry portion of nanofillers selected from the group consisting of silicates or sheet silicates, natural or modified by organic ions, silicas and combinations thereof;
c) from 0.01% to 5.0% by weight of said dry portion of nanofibers selected from the group consisting of rice husks, rice straw, soybean hulls, sugarcane bagasse, and combinations thereof;
d) from 0.0% to 50.0% by weight of said dry portion of other natural polymers chemically modified or unmodified or semi-synthetic, selected from the group consisting of starches and modified starches, galactomannans, pectins, cyclodextrins, water-soluble modified celluloses, chitosan, saccharide polymers of microbial origin, and combinations thereof; and
e) up to 1.6% by weight relative to the weight of xanthan of an anti-caking agent;
2) a wet portion, comprising:
a) from 2.0% to 60.0% by weight of said wet portion of wetting and dispersing agents, comprising i) lipophilic agents selected from the group consisting of edible oils and liquid lipids, vegetable oils of rice, soybean, sunflower, canola, peanut and corn, coconut, nuts, almonds and edible nuts, copaiba, and grape seed; and ii) hydrophilic agents selected from the group consisting of propylene glycol and polyethylene glycol, glycerin, glycerol, sorbitol, and combinations thereof;
b) from 0.5% to 2.0% by weight of said wet portion of antifoams selected from the group consisting of edible vegetable oils, emulsifiers, and combinations thereof, said emulsifiers selected from the group consisting of sorbitan trioleate and sorbitan tristearate;
c) from 0.0% to 2.0% by weight of said wet portion of emulsifiers selected from the group consisting of esterified mono and diglycerides, sorbitan esters, polyoxyethylene esters, polyoxyethylene sorbitan esters, and lecithins;
d) from 0.5% to 1.5% by weight of said wet portion of antioxidants selected from the group consisting of primary antioxidants and chelators, and synergists selected from the group consisting of butylated hydroxytoluene (BHT) and butylated hydroxyanisole (BHA), ascorbic acid and erythorbic acid and their salts, respectively, and combinations thereof;

e) acidity regulators or alkalizing agents, liquid or in solution, selected from inorganic bases and pharmaceutically acceptable low molecular weight amine bases, selected from the group consisting of sodium hydroxide and triethanolamine, for pH adjustment in the range of 6.0 to 7.5;

f) from 0.3% to 1.5% by weight relative to total weight of said composition, of preservatives, alone or in combination, selected from methyl and ethyl paraben, sorbic acid and sodium or potassium sorbate;

g) from 90% to 96% by weight relative to the total weight of the composition, of water and alcohol; and h) from 3.0% to 40% by weight relative to the total weight of the composition of at least one topical, liquid or solubilized anesthetic, selected from the group consisting of benzocaine, tetracaine, procaine, lidocaine, ropivacaine, bupivacaine, prilocaine, articaine, and combinations thereof.

12. The filmogenic composition according to claim 11, wherein the anti-caking agent is tricalcium phosphate.

13. The filmogenic composition according to claim 11, wherein the topical anesthetic is used in combination with anti-microbial or anti-inflammatory agents.

14. The filmogenic composition according to claim 11, wherein the saccharide polymers of microbial origin are selected from the group consisting of dextran and gellan.

15. The filmogenic composition according to claim 11, wherein said composition is mixed and submitted to a continuous casting process to produce films, strips or tapes of topical anesthetic bioadhesives.

16. A topical anesthetic bioadhesive (TAB) for controlled release of active principles, comprising a bioadhesive in the form of films, strips or tapes obtained from processing the composition according to claim 11.

17. The topical anesthetic bioadhesive (TAB) according to claim 16, wherein said bioadhesive comprises one single layer.

18. The topical anesthetic bioadhesive (TAB) according to claim 16, wherein said bioadhesive comprises an inner, anesthetic-containing layer and an anesthetic-free outer layer.

19. The bioadhesive according to claim 18, wherein said outer layer comprises a xanthan or a low or medium crystallinity polyhydroxyalkanoate (PHA), or hydroxymethylpropylcellulose phthalate.

20. The bioadhesive according to claim 19, wherein said outer layer xanthan is selected from the group consisting of xanthan gums produced by *Xanthomonas arboricola* pathovar *pruni*, *Xanthomonas campestris* pathovars *campestris* and manihotis, and combinations thereof.

* * * * *

UNITED STATES PATENT AND TRADEMARK OFFICE
CERTIFICATE OF CORRECTION

PATENT NO. : 10,722,586 B2
APPLICATION NO. : 15/525481
DATED : July 28, 2020
INVENTOR(S) : Vendruscolo et al.

It is certified that error appears in the above-identified patent and that said Letters Patent is hereby corrected as shown below:

On the Title Page

At item (12) please change:
"VENDRUSCULO et al."

To:
-- VENDRUSCOLO et al. --

And;

At item (72) Inventors: please change:
"Claire Tondo Vendrusculo, Ribeirão Preto (BR); Angelita Da Silveira Moreira, Pelotas (BR); Adriana Fernandes Da Silva, Pelotas (BR); Evandro Piva, Pelotas (BR); Wellington Luiz De Oliveira Rosa, Pelotas (BR); Francisco Augusto Burket Del Pino, Pelotas (BR)"

To:
-- Claire Tondo Vendruscolo, Ribeirão Preto (BR); Angelita Da Silveira Moreira, Pelotas (BR); Adriana Fernandes Da Silva, Pelotas (BR); Evandro Piva, Pelotas (BR); Wellington Luiz De Oliveira Rosa, Pelotas (BR); Francisco Augusto Burket Del Pino, Pelotas (BR) --

Signed and Sealed this
Twenty-ninth Day of September, 2020

Andrei Iancu
*Director of the United States Patent and Trademark Office*